United States Patent [19]

Berg

[11] Patent Number: 4,935,102
[45] Date of Patent: Jun. 19, 1990

[54] SEPARATION OF 2,3-BUTANEDIOL FROM PROPYLENE GLYCOL BY AZEOTROPIC DISTILLATION

[75] Inventor: Lloyd Berg, 1314 S. Third Ave., Bozeman, Mont. 59715

[73] Assignee: Lloyd Berg, Bozeman, Mont.

[21] Appl. No.: 457,868

[22] Filed: Dec. 27, 1989

[51] Int. Cl.$^5$ .......................... B01D 3/36; C07C 29/82
[52] U.S. Cl. .......................................... 203/58; 203/60; 203/62; 203/63; 203/64; 203/69; 568/868
[58] Field of Search .................... 203/58, 62, 63, 64, 203/60, 69, 44; 568/868

[56] References Cited

U.S. PATENT DOCUMENTS

| | | | |
|---|---|---|---|
| 2,389,263 | 11/1945 | Liebmann et al. | 568/868 |
| 2,865,819 | 12/1958 | Hagemeyer et al. | 203/69 |
| 3,809,724 | 5/1974 | Golden | 203/62 |
| 4,021,311 | 5/1977 | Becker | 203/60 |
| 4,057,471 | 11/1977 | Chueh | 203/69 |

FOREIGN PATENT DOCUMENTS 331054  4/1972  U.S.S.R. ................. 203/64

*Primary Examiner*—Wilbur Bascomb

[57] ABSTRACT

A complex mixture of polyols cannot be easily separated by atmospheric or reduced pressure distillation because of the closeness of their boiling points. A mixture of polyols can be readily separated by azeotropic distillation. Typical effective agents are: p-xylene for propylene glycol from 2,3-butanediol and 1,2-butanediol; diisobutyl ketone for ethylene glycol from 1,2-butanediol and 1,3-butanediol; dipentene for glycerine from triethylene glycol and 1,2,4-butanetriol; propylene glycol isobutyl ether for 2,3-butanediol from propylene glycol.

2 Claims, No Drawings

SEPARATION OF 2,3-BUTANEDIOL FROM PROPYLENE GLYCOL BY AZEOTROPIC DISTILLATION

FIELD OF THE INVENTION

This invention relates to a method for separating mixtures of polyols one from another using certain organic compounds as the agent in azeotropic distillation.

DESCRIPTION OF PRIOR ART

Azeotropic distillation is the method of separating close boiling compounds from each other by carrying out the distillation in a multiplate rectification column in the presence of an added liquid, said liquid forming an azeotrope with one or both of the compounds to be separated. Its presence on each plate of the rectification column alters the relative volatility in a direction to make the separation on each plate greater and thus require either fewer plates to effect the same separation or make possible a greater degree of separation with the same number of plates. The azeotrope forming agent is introduced with the feed to a continuous column. The azeotrope forming agent and the more volatile component are taken off as overhead product and the less volatile component comes off as bottoms product. The usual methods of separating the azeotrope former from the more volatile component are cooling and phase separation or solvent extraction.

In the hydrocracking of higher carbohydrates such as glucose, sorbitol or sucrose, the molecule is broken into fragments of lower molecular weight to form compounds which belong to the glycol or polyol family. Some of the resulting polyols boil so close to one another that their separation by ordinary rectification is difficult. The relative volatility is so low that a large number of theoretical plates are required to produce high purity polyols.

For instance, two of the close boiling glycols encountered in this process are 2,3-butanediol, b.p.=182° C. and propylene glycol, b.p.=187° C. and these two have a relative volatility of 1.25. The difficulty of separating these two by rectification can be shown by the data presented in Table 1.

TABLE 1

| Plates Required To Effect Separation In 99% Purity | | |
|---|---|---|
| Relative Volatility | Theoretical Plates | Actual Plates, 75% Efficiency |
| 1.25 | 41 | 55 |
| 1.35 | 31 | 42 |
| 1.45 | 25 | 34 |
| 1.50 | 23 | 31 |
| 1.70 | 18 | 24 |

Table 1 shows that rectification of 2,3-butanediol from propylene glycol in 99% purity requires 55 actual plates. Using azeotropic distillation with an agent yielding a relative volatility of 1.7 would require only 24 actual plates. Thus, azeotropic distillation would be an attractive method of effecting the separation of these two glycols if agents can be found that (1) will increase the relative volatility of 2,3-butanediol to propylene glycol and (2) are easy to recover from the 2,3-butanediol.

Azeotropic distillation typically requires from one to five parts as much agent as propylene glycol being boiled up in the column which increases the heat requirement as well as larger diameter plates to accomodate the increased liquid and vapor in the column.

The catalytic hydrocracking of sorbitol gave a mixture of polyols having the composition shown in Table 2.

TABLE 2

| Polyols Produced By Hydrocracking Of Sorbitol | | |
|---|---|---|
| Compound | Weight Percent | Boiling Point, °C. |
| 2,3-Butanediol | 3.5 | 182 |
| Propylene glycol | 16.5 | 187 |
| 1,2-Butanediol | 2.0 | 192 |
| Ethylene glycol | 25.2 | 198 |
| 1,3-Butanediol | 2.7 | 206 |
| 2,3-Hexanediol | — | 206 |
| 1,2-Pentanediol | — | 210 |
| 1,4-Pentanediol | — | 220 |
| 1,4-Butanediol | 2.1 | 230 |
| 1,5-Pentanediol | 0.1 | 242 |
| Diethylene glycol | 2.2 | 245 |
| 1,6-Hexanediol | — | 250 |
| Triethylene glycol | 2.1 | 285 |
| Glycerine | 38.8 | 290 |
| 1,2,4-Butanetriol | 4.8 | 190/18 mm. |
| | 100.0 | |

The principal products were 16.5% propylene glycol, 25.2% ethylene glycol and 38.8% glycerine. To be of commercial value in most uses, these compounds must be of high purity. Table 2 shows the other polyols that resulted are 3% 2,3-butanediol, 2% 1,2-butanediol, 2.7% 1,3-butanediol, 2.1% 1,4-butanediol, 0.1% 1,5-pentanediol, 2.2% diethylene glycol, 2.1% triethylene glycol and 4.8% 1,2,4-butanetriol. Table 2 also shows how close these minor polyols boil to propylene glycol, ethylene glycol and glycerine. When this mixture was subjected to rectification, either at one atm. or at reduced pressure, separation to high purity compounds could not be attained.

Chueh, U.S. Pat. No. 4,057,471 used aromatic hydrocarbons as the agent in the azeotropic separation of ethylene glycol and propylene glycol from carboxylic esters. He did not separate one glycol from another glycol. Becker, U.S. Pat. No. 4,021,311 used 1,2,3-trimethyl benzene as the azeotropic agent to separate propylene glycol from carboxylic acid esters.

OBJECTIVE OF THE INVENTION

The objective of this invention is to provide a process or method of azeotropic distillation that will enhance the relative volatility of one polyol from another in their separation in a rectification column. It is a further object of this invention to identify organic compounds which in addition to the above constraints, are stable, can be separated from the polyols being purified and can be recycled to the azeotropic distillation and reused with little decomposition.

SUMMARY OF THE INVENTION

The objects of this invention are provided by a process for separating one polyol from another polyol which entails the use of certain organic compounds in an azeotropic distillation process.

DETAILED DESCRIPTION OF THE INVENTION

I have discovered that certain organic compounds will effectively enhance the relative volatility in azeotropic distillation of one glycol from another glycol when they occur together as a close boiling mixture. In the mixture of polyols shown in Table 2, the major products are propylene glycol, ethylene glycol and glycerine. To be of commercial value, these compounds must be obtained in high purity. With this mixture, I have divided the separation into six parts. They are: the separation of 2,3-butanediol (182) from propylene glycol (187); propylene glycol (187) from 1,2-butanediol (192); 1,2-butanediol (192) from ethylene glycol (198); ethylene glycol (198) from 1,3-butanediol (206); triethylene glycol (285) from glycerine (290) and glycerine (290) from 1,2,4-butanetriol (300+).

2,3-Butanediol From Propylene Glycol.

Table 3 lists the effective azeotrope forming agents for the separation of 2,3-butanediol from propylene glycol. The most effective agents are propylene glycol isobutyl ether, tetrahydro furfuryl alcohol and N,N-dimethylacetamide. The data in Table 3 indicates, for example, that one part of propylene glycol isobutyl ether mixed with one part of the 2,3-butanediol - propylene glycol mixture gives a relative volatility of 1.70 and boils at 165° C. 640 mm Hg.

TABLE 3

Effective Agents For Separating Propylene Glycol From 2,3-Butanediol

| Compound | Relative Volatility | Azeotrope, B.P., °C. @ 640 mm |
|---|---|---|
| Propylene glycol isobutyl ether | 1.70 | 165 |
| Tetrahydro furfuryl alcohol | 1.50 | 174 |
| N,N-dimethylacetamide | 1.50 | 173 |
| Ethylene glycol diethyl ether | 1.46 | 124 |
| Diethylene glycol diethyl ether | 1.40 | 175 |
| 2-Methoxyethyl ether | 1.40 | 163 |
| Ethylene glycol n-butyl ether | 1.40 | 168 |
| Diacetone alcohol | 1.39 | 159 |
| Ethyl n-butyl ketone | 1.36 | 147 |

TABLE 4

| Potential Agents That Are Ineffective | |
|---|---|
| Adiponitrile | Isophorone |
| Butyl benzoate | Phenyl ether |
| Isobutyl heptyl ketone | Ethylene glycol phenyl ether |

TABLE 4-continued

| Potential Agents That Are Ineffective | |
|---|---|
| 2-Undecanone | Hexyl ether |
| 2-Octanone | Anisole |
| Cyclohexanone | Dimethylformamide |
| Propylene glycol propyl ether | Ethylene glycol butyl ether acetate |
| Propylene glycol butyl ether | Ethylene glycol diacetate |
| Glycerol triacetate | Dipropylene glycol methyl ether |
| Diethylene glycol methyl ether | Ethylene glycol hexyl ether |
| Acetophenone | Diethyl oxalate |
| 2-Octanol | Benzyl alcohol |
| Methyl benzyl alcohol | Isooctyl alcohol |
| n-Decanol | 2-Ethyl-1-hexanol |
| Diisobutyl carbinol | Phenethyl alcohol |
| n-Octanol | 2-Hydroxyacetophenone |
| Isobornyl methyl ether | Nitrobenzene |

Table 4 lists a number of compounds which proved to be ineffective as agents in this separation.

TABLE 5

Effective Agents For Separating Propylene Glycol From 2,3-Butanediol

| Agent | Time hrs. | Azeo. Temp. °C. | Overhead % 2,3-Bu | Comp. % PrGl | Bottoms % 2,3-Bu | Comp. % PrGl | % PG in Overhead | Relative Volatility |
|---|---|---|---|---|---|---|---|---|
| Toluene | 5 | 105 | 13.5 | 86.5 | 42.6 | 57.4 | 4 | 1.05 |
| Ethylbenzene | 5.5 | 127 | 2.4 | 97.6 | 42.3 | 57.7 | 15 | 1.12 |
| p-Xylene | 6 | 130 | 2.0 | 98.0 | 43.2 | 56.8 | 18 | 1.13 |
| m-Xylene | 2 | 129 | 2.1 | 97.9 | 37.5 | 62.5 | 17 | 1.12 |
| o-Xylene | 7 | 133 | 5.6 | 94.4 | 42.1 | 57.9 | 18 | 1.09 |
| Cumene | 6 | 132 | 7.2 | 92.8 | 38.4 | 61.6 | 17 | 1.07 |
| Mesitylene | 3 | 142 | 10.5 | 89.5 | 39.8 | 60.2 | 25 | 1.06 |

Table 5 lists toluene, ethylbenzene, p-xylene, m-xylene, o-xylene, cumene and mesitylene which are effective azeotrope forming agents to separate 2,3-butanediol from propylene glycol. While possessing a relative volatility somewhat lower than those in Table 3, they have the advantage of forming a two phase overhead product which enables separation of the 2,3-butanediol from the aromatic hydrocarbons by simple decantation.

Propylene Glycol From 2,3-Butanediol And 1,2-Butanediol.

Table 6 shows that the same agents except toluene are also effective in separating propylene glyco from 1,2-butanediol with the propylene glycol coming off as a two phase overhead even when both of these glycols are present.

TABLE 6

Effective Agents For Separating Propylene Glycol From Both 2,3-Butanediol And 1,2-Butanediol

| Agent | Azeo Temp. | Time hrs. | OVERHEAD | | | BOTTOMS | | | % PG in Overhead | Relative Volatility |
| | | | % 2,3 Bu | % PG | % 1,2 Bu | % 2,3 Bu | % PG | % 1,2 Bu | | |
|---|---|---|---|---|---|---|---|---|---|---|
| Ethylbenzene | 126 | 6 | 0.9 | 97.8 | 1.3 | 8.6 | 51.5 | 39.9 | 13 | 1.13 |
| p-Xylene | 129 | 9 | 0.5 | 99.5 | 0 | 9.1 | 50.7 | 40.2 | 10 | 1.19 |
| m-Xylene | 130 | 4 | 0.9 | 99.1 | 0 | 44.6 | 42.7 | 12.7 | 5 | 1.17 |
| o-Xylene | 131 | 3 | 0.9 | 99.1 | 0 | 49.9 | 41.3 | 8.8 | 10 | 1.18 |
| Cumene | 126 | 5 | 0.8 | 99.2 | 0 | 40.7 | 50.5 | 8.8 | 22 | 1.17 |
| Mesitylene | 141 | 5 | 2.5 | 97.5 | 0 | 43.1 | 48.2 | 8.7 | 20 | 1.15 |

The effective compounds are ethylbenzene, p-xylene m-xylene, o-xylene, cumene and mesitylene. While these all have about the same relative volatility, the percent propylene glycol in the overhead varies considerably depending on the agent. Cumene with 22% propylene glycol in the overhead is the best, m-xylene with only 5% is the poorest.

The data in Table 5 was obtained in a 30 theoretical plate packed rectification column. It lists the time run at total reflux, the overhead temperature in Celcius degrees, the overhead composition at the end of the reflux period, the weight percent of propylene glycol in the azeotrope and the relative volatility of propylene glycol to 2,3-butanediol with each agent. Table 6 lists similar data from the same column when the mixture contained 1,2-butanediol as well as 2,3-butanediol.

Ethylene Glycol From 1,2-Butanediol And 1,3-Butanediol.

1,2-Butanediol and 1,3-Butanediol are the glycols boiling closest below and above ethylene glycol, see Table 2. In Table 7 are listed the agents that are effective in separating ethylene glycol from both 1,2-butanediol and 1,3-butanediol. The data in Table 7 was obtained in a vapor liquid equilibrium still.

isoamyl ketone, isobutyl heptyl ketone and 2,6-dimethyl-4-heptanone and the glycol ether 2-methoxyethyl ether.

Table 8 lists a number of effective agents whose relative volatilities were obtained in a 30 plate rectification column at 640 mm.Hg pressure. The temperature of the azeotrope is listed as well as the overhead and bottoms composition and the percent of ethylene glycol in the overhead. The effective agents are the aromatic hydrocarbons o-xylene, m-xylene, p-xylene, ethylbenzene, cumene and mesitylene. Diisobutyl ketone was also investigated in the rectification column. Each agent was evaluated using the binary mixture of 1,2-butanediol and ethylene glycol and the ternary containing 1,2-butanediol, ethylene glycol and 1,3-butanediol. The results indicate that the separation of ethylene glycol from mixtures containing both 1,2-butanediol and 1,3-

TABLE 7

Effective Agents For Separating Ethylene Glycol From 1,2-Butanediol and 1.3-Butanediol, Vapor-Liquid Equil. Still

| Agent | Temp. | Press. mm Hg | OVERHEAD | | | BOTTOMS | | | Relative Volatility | |
|---|---|---|---|---|---|---|---|---|---|---|
| | | | % EG | % 1,2Bu | % 1,3Bu | % EG | % 1,2Bu | % 1,3Bu | EG:1,2Bu | EG:1,3Bu |
| 3-Heptanone | 108 | 60 | 99.9 | 0.1 | — | 59.7 | 40.3 | — | 10+ | |
| 3-Heptanone | 112 | 60 | 94.9 | 0 | 5.1 | 44.4 | 34.4 | 21.2 | 10+ | 8.9 |
| Cyclohexanone | 117 | 60 | 100 | 0 | — | 56.4 | 43.6 | — | 10+ | |
| Cyclohexanone | 80 | 50 | 70.7 | 13.9 | 15.4 | 54.3 | 32.3 | 13.4 | 3.0 | 1.1 |
| Diisobutylketone | 124 | 60 | 100 | 0 | — | 62 | 38 | — | 1.27 | |
| Diisobutylketone | 125 | 60 | 95.9 | 0 | 4.1 | 50.7 | 34.0 | 15.3 | 1.71 | 1.26 |
| Methyl isoamylketone | 113 | 60 | 99.9 | 0.1 | — | 66.1 | 33.9 | — | 10+ | |
| Methyl isoamyl ketone | 118 | 60 | 94.3 | 0 | 5.7 | 46.7 | 27.1 | 26.2 | 10+ | 9.3 |
| Isobutylheptyl ketone | 131 | 60 | 73.6 | 26.3 | — | 21.6 | 78.4 | — | 10.2 | |
| Isobutyl heptylketone | 140 | 60 | 67.4 | 20.1 | 12.5 | 60.8 | 26.8 | 12.4 | 1.5 | 1.1 |
| 2-Methoxyethyl ether | 130 | 60 | 99.9 | 0.1 | — | 71.7 | 28.3 | — | 10+ | |
| 2-Methoxyethyl ether | 132 | 60 | 99.8 | 0.1 | 0.1 | 60.8 | 21.7 | 17.5 | 10+ | 10+ |
| 2,6-diMe-4-heptanone | 134 | 60 | 99.9 | 0.1 | — | 71.2 | 28.8 | — | 10+ | |
| 2,6-diMe-4-heptanone | 132 | 60 | 93.7 | 0.1 | 6.3 | 50.4 | 25.0 | 24.6 | 10+ | 7.3 |

TABLE 8

Effective Agents For Separating Ethylene Glycol From Both 1,2-Butanediol and 1,3-Butanediol

| Agent | Azeo Temp | Time hrs. | OVERHEAD | | | BOTTOMS | | | % EG in Overhead | Relative Volatility | |
|---|---|---|---|---|---|---|---|---|---|---|---|
| | | | % EG | %12Bu | %13Bu | % EG | %12Bu | %13Bu | | EG:1,2Bu | EG:1,3Bu |
| o-Xylene | 131 | 2.5 | 85.9 | 14.1 | — | 53.3 | 46.7 | — | 22 | 1.06 | |
| o-Xylene | 130 | 5 | 92 | 8 | 0 | 41.2 | 37.6 | 21.2 | 9 | 1.1 | 10+ |
| m-Xylene | 130 | 6 | 95.3 | 4.7 | — | 49.9 | 50.1 | — | 10 | 1.11 | |
| m-Xylene | 130 | 4 | 95.2 | 4.8 | 0 | 44.6 | 34.6 | 20.8 | 22 | 1.11 | 10+ |
| p-Xylene | 130 | 5 | 98.4 | 1.6 | — | 48.1 | 51.9 | — | 10 | 1.15 | |
| p-Xylene | 130 | 9 | 94.8 | 5.2 | 0 | 48.5 | 33.4 | 21.1 | 8 | 1.11 | 10+ |
| Ethyl benzene | 121 | 5 | 99.9 | 0.1 | — | 42.3 | 57.7 | — | 7 | 1.27 | |
| Ethyl benzene | 125 | 6 | 99.9 | 0.1 | 0 | 43.3 | 35.4 | 21.3 | 15 | 1.27 | 10+ |
| Cumene | 114 | 5 | 99.9 | 0.1 | — | 61.6 | 38.4 | — | 20 | 1.26 | |
| Cumene | 120 | 8 | 99.3 | 0.7 | 0 | 48.6 | 21.6 | 29.8 | 10 | 1.18 | 10+ |
| Mesitylene | 126 | 5 | 99.1 | 0.9 | — | 48.3 | 51.7 | — | 20 | 1.17 | |
| Mesitylene | 129 | 8 | 98 | 2 | 0 | 49.8 | 18.2 | 32.0 | 10 | 1.15 | 10+ |
| Diisobutylketone | 153 | 12 | 99.8 | 0.1 | 0.1 | 32.2 | 49.2 | 18.6 | 15 | 1.31 | 1.26 |
| Diisobutylketone | 151 | 11 | 99.1 | 0.1 | — | 41.9 | 58.1 | — | 13 | 1.27 | |

The relative volatilities found are very high. When too high to measure acturately, 10+ is indicated. The data in Table 7 was obtained at 50-60 mm.Hg absolute pressure and the temperature shown corresponds to that pressure. The most effective compounds are the ketones 3-heptanone, cyclohexanone, diisobutyl ketone, methyl butanediol is just as good as with 1,2-butanediol and ethylene glycol.

Glycerine From Triethylene Glycol And 1,2,4-Butanetriol.

Triethylene glycol and 1,2,4-butanetriol are the polyols boiling closest to glycerine, see Table 1.

TABLE 9

Effective Agents For Separating Glycerine From Both Triethylene Glycol and 1,2,4-Butanetriol

| Agent | Azeo. Temp. | Time hrs. | OVERHEAD | | | BOTTOMS | | | % TEG in Overhead | Realtive Volatility | |
|---|---|---|---|---|---|---|---|---|---|---|---|
| | | | % TEG | % Gly | %124Bu | % TEG | % Gly | % 124Bu | | Gly:TEG | Gly:124Bu |
| o-Xylene | 96 | 1.5 | 53 | 47 | — | 67.4 | 32.6 | — | 20 | 1.8 | |
| Isopropylcyclohexane | 76 | 4 | 5.2 | 94.8 | 0 | 15.5 | 81.1 | 3.4 | 65 | 3.5 | 10+ |

TABLE 9-continued

Effective Agents For Separating Glycerine From Both Triethylene Glycol and 1,2,4-Butanetriol

| Agent | Azeo. Temp. | Time hrs. | OVERHEAD | | | BOTTOMS | | | % TEG in Overhead | Realtive Volatility | |
|---|---|---|---|---|---|---|---|---|---|---|---|
| | | | % TEG | % Gly | %124Bu | % TEG | % Gly | % 124Bu | | Gly:TEG | Gly:124Bu |
| Alpha-Pinene | 103 | 2 | 99.1 | 0.9 | — | 96 | 4 | — | 40 | 4.9 | |
| 2,6-Dimethyl-4-heptanone | 112 | 4 | 3.5 | 96.5 | — | 2.8 | 97.2 | — | 10 | 1.2 | |
| m-Xylene | 106 | 1.3 | 0.4 | 99.6 | 0 | 11.6 | 86.6 | 1.8 | 10 | 10+ | 10+ |
| 2,2,4-Trimethyl-pentane | 91 | 1.5 | 2 | 98 | — | 4 | 96 | — | 15 | 2 | |
| Dipentene | 136 | 5 | 1 | 99 | — | 1.8 | 98.2 | — | 33 | 2.5 | |
| 2-Methoxyethyl-ether | 116 | 3 | 6.1 | 93.9 | — | 13.4 | 81.6 | — | 1 φ | 2.5 | |

TABLE 10

Data From Vapor-Liquid Equilibrium Still

| | Relative Volatility | |
|---|---|---|
| Agent | TEG:Gly | Gly:1,2,4-Bu |
| Ethylbenzene | 2.1 | 31 |
| o-Xylene | 1.7 | 17 |
| p-Xylene | 3.6 | 3 |
| Cumene | 1.8 | 23 |
| Diisobutyl ketone | 1.7 | 3.1 |

Tables 9 and 10 list the agents found to be effective in separating glycerine from these two polyols. The 1,2,4-butanetriol boils so much higher than glycerine that it poses no difficulty in separation. The relative volatility is too high to be measured accurately. All the agents listed in Table 9 except 2-methyoxyethyl ether form two phase azeotropes with glycerine. o-Xylene, isopropyl cyclohexane and alpha-pinene bring the triethylene glycol out as overhead. 2,6-Dimethyl-4-heptanone, m-xylene, dipentene and 2-methoxyethyl ether bring the glycerine out as overhead.

WORKING EXAMPLES

EXAMPLE 1

Thirty grams of 2,3-butanediol - propylene glycol mixture and 30 grams of ethylene glycol diethyl ether were charged to an Othmer type vapor-liquid equilibrium still and refluxed for four hours. Analysis by gas chromatography gave a vapor composition of 54.5% 2,3-butanediol, 45.5% propylene glycol; a liquid composition of 45.1% 2,3-butanediol, 54.9% propylene glycol. This indicates a relative volatility of 2,3-butanediol to propylene glycol of 1.46.

EXAMPLE 2

A two foot long rectification column packed with Berl saddles was calibrated with m-diiopropylbenzene and p-diiopropylbenzene which possesses a relative volatility of 1.14 and found to have 2.3 theoretical plates. A solution comprising 50 grams of 2,3-butanediol, 50 grams of propylene glycol and 50 grams of propylene glycol isobutyl ether was placed in the stillpot and heated. After two hours of refluxing at total reflux, analysis was made by gas chromatography. The overhead composition was 88% 2,3-butanediol, 12% propylene glycol and the stillpot analysis was 18% 2,3-butanediol, 82% propylene glycol. Using these compositions in the Fenske equation with the number of theoretical plates in the column being being 2.3, gave an average relative volatility of 1.69 for each theoretical plate.

EXAMPLE 3

A four foot rectification column packed with stainless steel helices was calibrated with m-xylene and p-xylene which possesses a relative volatility of 1.11 and found to have thirty theoretical plates. A solution comprising 50 grams of ethylene glycol, 40 grams of 1,2-butanediol, 20 grams of 1,3-butanediol and 100 grams of ehtylbenzene was placed in the stillpot and heated. After six hours of refluxing at total reflux, the overhead composition was 99.9% ethylene glycol, 0.1% 1,2-butanediol, 0% 1,3-butanediol and the bottoms composition was 43.3% ethylene glycol, 35.4% 1,2-butanediol and 21.3% 1,3-butanediol. This gives a relative volatility of ethylene glycol to 1,2-butanediol of 1.27 of ethylene glycol to 1,3-butanediol of 10+. These data are shown in Table 8.

EXAMPLE 4

To the four foot rectification column described in Example 3 was charged 20 grams of triethylene glycol, 20 grams of glycerine, 10 grams of 1,2,4-butanetriol and 100 grams of isopropyl cyclohexane. The overhead temperature was 76° C., the bottoms was 165° C. After four hours at total reflux, an overhead sample comprising 35% isopropyl cyclohexane, 65% glycols was taken. The glycol layer composition was 5.2% triethylene glycol, 94.8% glycerine, 0% 1,2,4-butanetriol and the bottoms composition was 15.5% triethylene glycol, 81.1% glycerine and 3.4% 1,2,4-butanetriol. This is a relative volatility of glycerine to triethylene glycol of 3.5. These data are shown in Table 9.

EXAMPLE 5

Twenty grams of triethylene glycol, 20 grams of glycerine, 5 grams of 1,2,4-butanetriol and 40 grams of diisobutyl ketone were charged to the vapor-liquid equilibrium still and refluxed for three hours. The vapor composition was 78.3% triethylene glycol, 21.2% glycerine and 0.5% 1,2,4-butanetriol and the liquid composition was 66.7% triethylene glycol, 31% glycerine and 2.3% 1,2,4-butanetriol which is a relative volatility of triethylene glycol to glycerine of 1.7 of glycerine to 1,2,4-butanetriol of 3.1. This data is shown in Table 10 and shows that agents were found which could take either glycerine or triethylene glycol out as overhead product.

I claim:

1. A method for recovering 2,3-butanediol from a mixture of 2,3-butanediol and propylene glycol which comprises distilling a mixture of 2,3-butanediol and propylene glycol in a rectification column in the presence of an azeotrope forming agent, recovering the 2,3-butanediol and the azeotrope forming agent as overhead product, obtaining the propylene glycol from the stillpot, wherein said azeotrope forming agent consists of one material selected from the group consisting of propylene glycol isobutyl ether, tetrahydro furfuryl alcohol, N,N-dimethylacetamide, ethylene glycol diethyl ether, diethylene glycol diethyl ether, 2-methoxyethyl ether, ethylene glycol n-butyl ether, diacetone alcohol and ethyl n-butyl ketone.

2. A method for recovering 2,3-butanediol from a mixture of 2,3-butanediol and propylene glycol which comprises distilling a mixture of 2,3-butanediol and propylene glycol in a rectification column in the presence of an azeotrope forming agent, recovering the 2,3-butanediol and the azeotrope forming agent as overhead product, said overhead product forming two liquid layers separating the 2,3-butanediol from the azeotrope forming agent by decantation of the two liquid layers, obtaining the propylene glycol from the stillpot, wherein said azeotrope forming agent consists of one material selected from the group of aromatic hydrocarbons consisting of ethylbenzene, p-xylene, m-xylene, o-xylene, cumene and mesitylene.

* * * * *